(12) United States Patent
Israël et al.

(10) Patent No.: US 6,872,751 B2
(45) Date of Patent: Mar. 29, 2005

(54) COMPOSITION AND METHOD FOR AUGMENTING OR RESTORING THE PRODUCTION OF FETAL PROTEIN IN PATIENT IN NEED THEREOF

(75) Inventors: Maurice Israël, Bures-sur-Yvette (FR); Sabine De La Porte, Versailles (FR); Philippe Fossier, Louvres (FR); Emmanuel Chaubourt, Vars (FR); Gérard Baux, Sainte-Genevieve-des-Bois (FR); Christiane Leprince, Gif-sur-Yvette (FR)

(73) Assignee: Centre National de la Recherche Scientifique - CNRS, Paris (FR)

( * ) Notice: Subject to any disclaimer, the term of this patent is extended or adjusted under 35 U.S.C. 154(b) by 0 days.

(21) Appl. No.: 10/133,435

(22) Filed: Apr. 29, 2002

(65) Prior Publication Data

US 2002/0164383 A1 Nov. 7, 2002

Related U.S. Application Data

(63) Continuation-in-part of application No. 10/009,198, filed as application No. PCT/FR00/01612 on Jun. 9, 2000.

(30) Foreign Application Priority Data

Jun. 11, 1999 (FR) .............................. 99 07742

(51) Int. Cl.$^7$ ........................ A61K 31/13; A61K 31/44; A61K 31/495; A61K 31/445; A61K 31/40
(52) U.S. Cl. ........................ 514/611; 514/642; 514/624; 514/634; 514/231.2; 514/509; 514/565
(58) Field of Search ................................ 514/611, 642, 514/624, 634

(56) References Cited

U.S. PATENT DOCUMENTS

| 5,789,447 | A | * | 8/1998 | Wink et al. .................. 514/611 |
| 5,885,621 | A | | 3/1999 | Head et al. |
| 6,153,186 | A | * | 11/2000 | Stamler et al. .......... 424/93.73 |

FOREIGN PATENT DOCUMENTS

| DE | 29709820 | | 7/1997 |
| EP | 0 870 763 | | 10/1998 |
| WO | WO 95/28377 | | 10/1995 |
| WO | WO 96/02241 | | 2/1996 |
| WO | WO 97/10265 | * | 3/1997 |
| WO | WO 97/25984 | | 7/1997 |
| WO | WO 97/33173 | | 9/1997 |
| WO | WO 97/37644 | * | 10/1997 |
| WO | WO 98/13358 | | 4/1998 |
| WO | WO 99/01427 | | 1/1999 |
| WO | WO 00/53191 | * | 9/2000 |

OTHER PUBLICATIONS

Kameya et al., The Journal of Biological Chemistry, 1999, vol. 274, No. 4, Issue of Jan. 22, pp. 2193–2200.*
"New Hope for people with Sickle Cell Anemia", Eleanor Mayfield, FDA Consumer, May 1996.*
"Sickle Cell Anemia", National Heart, Lung and Blood Institute, 1996.*
"Duchenne Muscular Dystrophies–Annual Condition Specific Review", Muscular Dystrophy Campaign, Sep. 2001.*
"Thalassemia–What is Thalassemia?", University of Rochester Medical Center, 2003.*
Shuichi Yamada: "Effects on ATP and amino acid mixtures on progressive muscular dystrophy," Sapporo Igaku Zasshi, 1965, pp. 284–297, vol. 27, XP002131218.
D.S. Bredt, "Endogenous nitric oxide synthesis: Biological functions and pathophysiology," Free Radical Research, 1999, pp. 577–596, 31/6, XP00213219.
J.W. Haycock et al., "Oxidative damage to muscle protein in Duchenne muscular dystrophy," Neuroreport, 1996, pp. 357–361, vol. 8, No. 1, Rapid Science Publishers, XP000879014.
D.S. Chao et al.: "Selective loss of sarcolemmal nitric oxide synthase in Becker muscular dystrophy," J. Exp. Med., 1996, pp. 609–618, vol. 184(2), The Rockefeller University Press, USA.
R. Lainé et al.: "Neuronal nitric oxide synthase isoforms.alpha.and.mu. are closely related calpain–sensitive proteins," Mol. Pharmacol., 1998, pp. 305–312, vol. 54(2), The American Society for Pharmacology and Experimental Therapeutics, USA.
A. Decrouy et al.: "Mini– and full–length dystrophin gene transfer induces the recovery of nitric oxide synthase at the sarcolemma of mdx4cv skeletal muscle fibers," Gene Therapy, 1998, pp. 59–64, vol. 5(1), Stockton Press, United Kingdom.
G.B. Azzena et al.: "Nitric oxide regenerates the normal colonic peristaltic activity in mdx dystrophic mouse," Neuroscience Letters, 1999, pp. 9–12, vol. 261, Elsevier Science Ireland Ltd., Ireland.

(Continued)

Primary Examiner—Vickie Kim
Assistant Examiner—Brian-Yong S. Kwon
(74) Attorney, Agent, or Firm—Burns, Doane, Swecker & Mathis, LLP

(57) ABSTRACT

The present invention relates to methods for prevention and/or treatment of diseases or conditions caused by deficiency in the adult isoform of a given protein wherein said method comprises administering to a patient in need thereof a composition containing NO or at least one compound able to release, induce and/or promote NO formation in cells, said administration resulting in augmenting or restoring the production of the fetal isoform of said protein in said patient.

4 Claims, 9 Drawing Sheets

OTHER PUBLICATIONS

G.D. Thomas et al.: "Impaired metabolic modulation of alpha–adrenergic . . . ," Proc. Natl. Acad. Sci. USA, 1998, pp. 15090–15095, vol. 95/25, The National Academy of Sciences, USA.

E. Chaubourt et al.: "Nitric oxide and L–arginine cause an accumulation of utrophin at the . . . " Neurobiology of Disease, 1999, pp. 499–507, vol. 6/6, Academic Press, USA.

W.H. Waugh et al.: "Evidence that L–arginine is a key amino acid in sickle cell anemia– . . . ", Nutr. Res. (N.Y.), 1999, pp. 501–508, vol. 19(4), Elsevier Science Inc., USA.

A.N. Schechter: "NO Therapy?," Journal of Clin. Investigation, 1997, pp. 955–956, vol. 100/5, USA.

C.A. Head et al.: "Low concentrations of nitric oxide increase oxygen affinity . . . ", J. Clin. Invest., 1997, pp. 1193–1198, vol. 100(5), The American Society for Clinical Investigation, Inc., USA.

S.P. Perrine et al.: "Butyrate–induced reactivation of the fetal globin genes . . . ", Experientia, Birkhäuser Verlag, 1993, pp. 133–137, vol. 49, No. 2, CH–4010, Basel/Switzerland.

R. Pacelli et al.: "Hydroxyurea reacts with heme proteins to generate nitric oxide," Lancet, 1996, p. 900, 347/9005.

C. Morris et al.: "Effects of L–arginine therapy on nitric oxide production in patients . . . ", Blood, (Nov. 15, 1998), p. 2858, vol. 92, No. 10, Suppl. 1 Part 1–2, Lippincott Williams & Wilkins, USA.

C.O. Enwonwu: "Increased metabolic demand for arginine in sickle cell anemia," Med. Sci. Res., 1989, pp. 997–998, vol. 17(23).

G.D. Sher et al.: "Extended therapy with intravenous arginine butyrate in patients with beta . . . ", New Eng. J. of Med., 1995, pp. 1606–1610, vol. 332/24, Massachusetts Medical Society, USA.

C.R. Morris et al.: "L–arginine therapy paradoxically decreases nitric oxide production in patients with sickle cell disease," Ped. Res., 1999, p. 876, vol. 45, No. 4, Part 2.

A.M. Atz et al.: "Inhaled nitric oxide in sickle cell disease with acute chest syndrome," Anesthesiology, 1997, pp. 988–990, vol. 87, No. 4, Lippincott–Raven Publishers, USA.

* cited by examiner

Fig.1
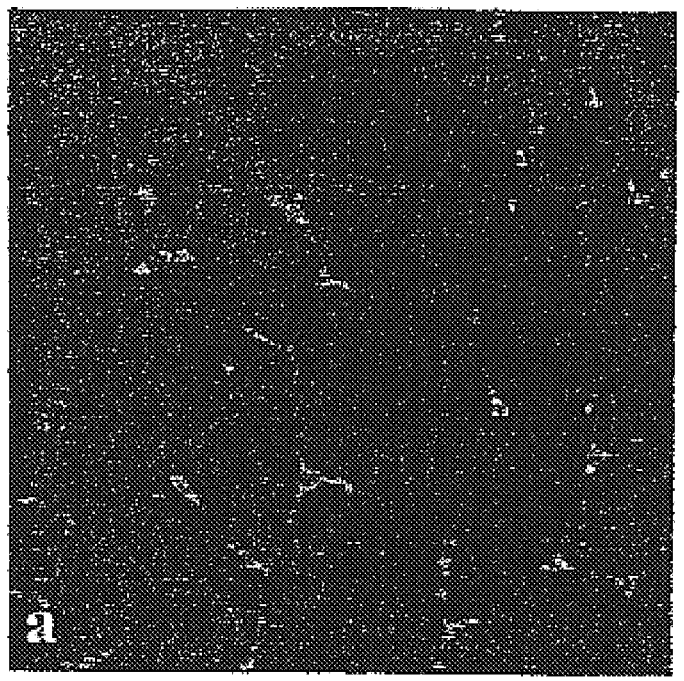
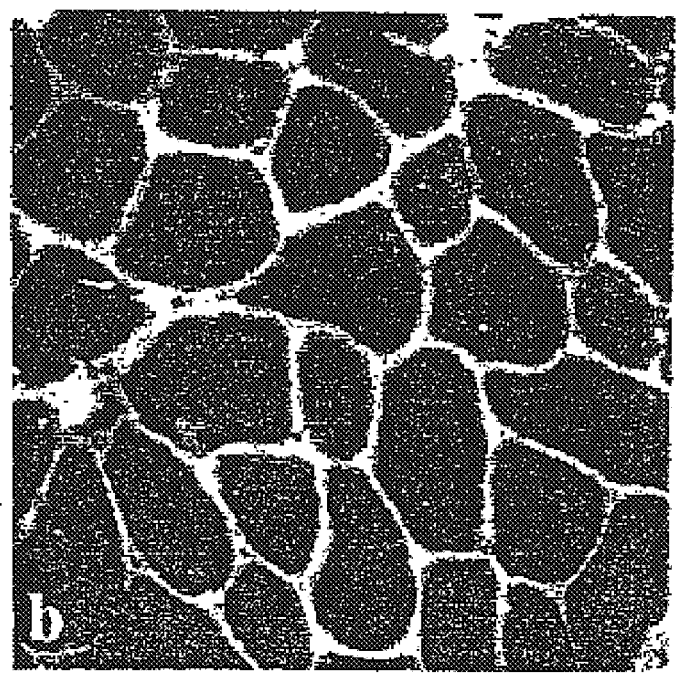

Fig.1 Suite
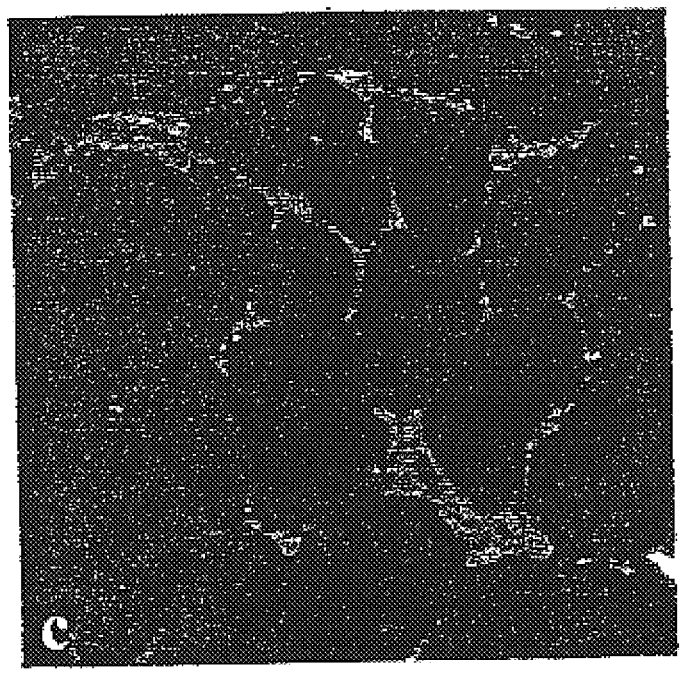
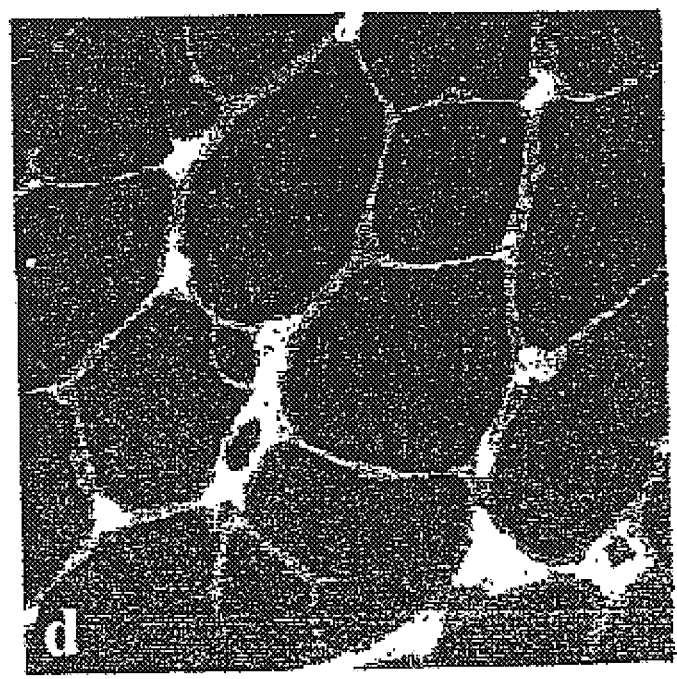

Fig.2 A NXLT
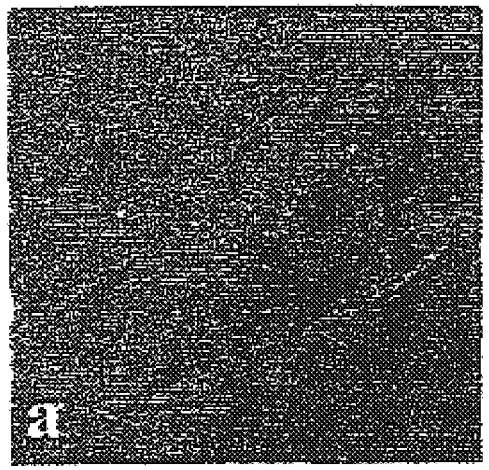
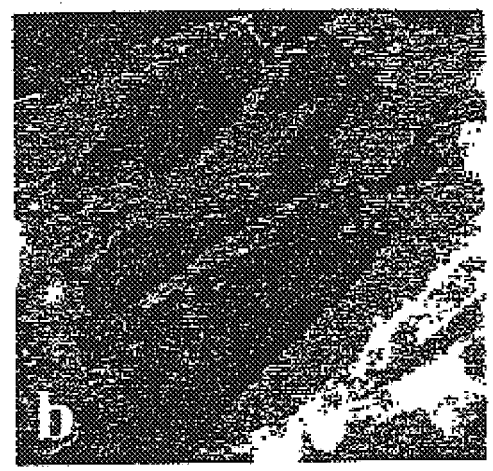
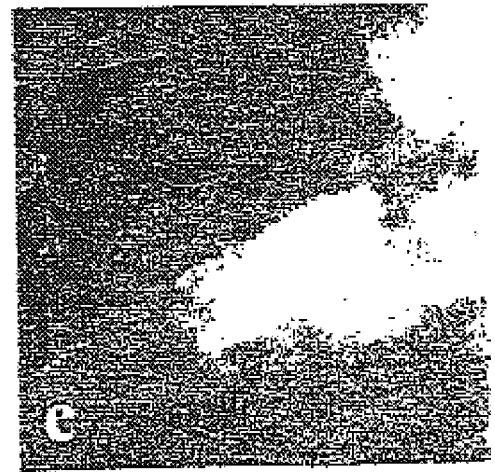

Fig.2 A NXLT Suite
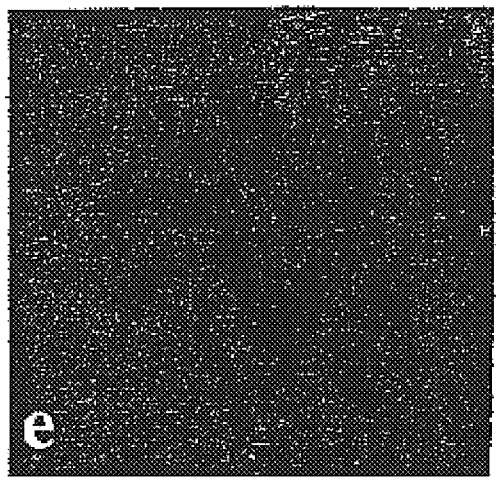

Fig.2 B XLT
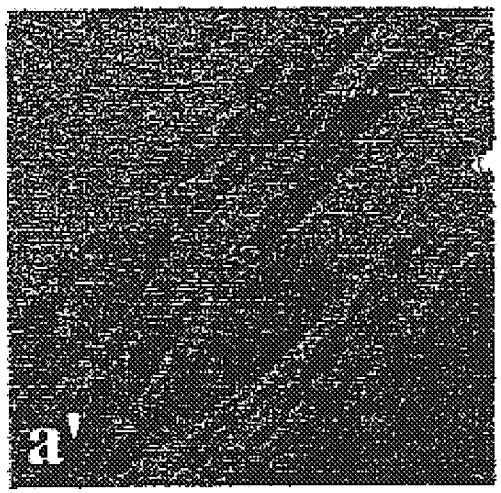
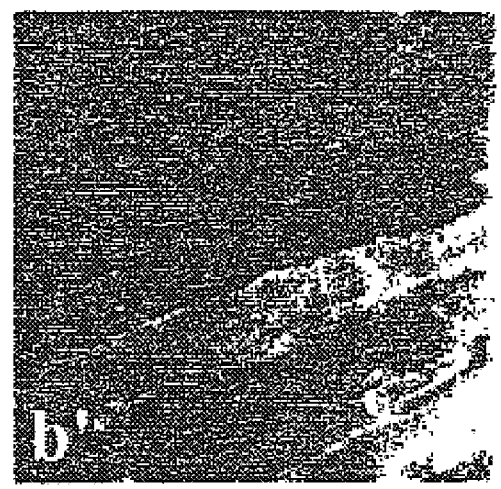
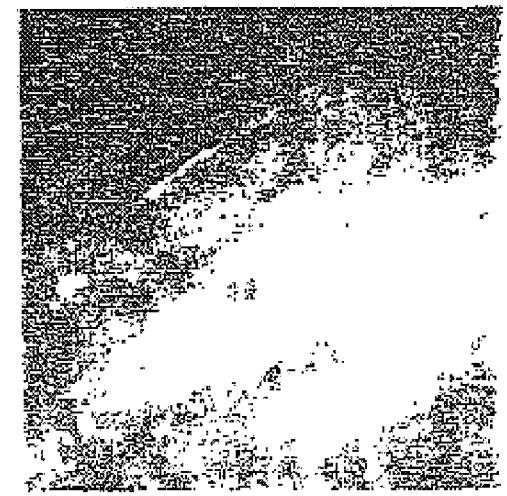

Fig.2 A NXLT Suite
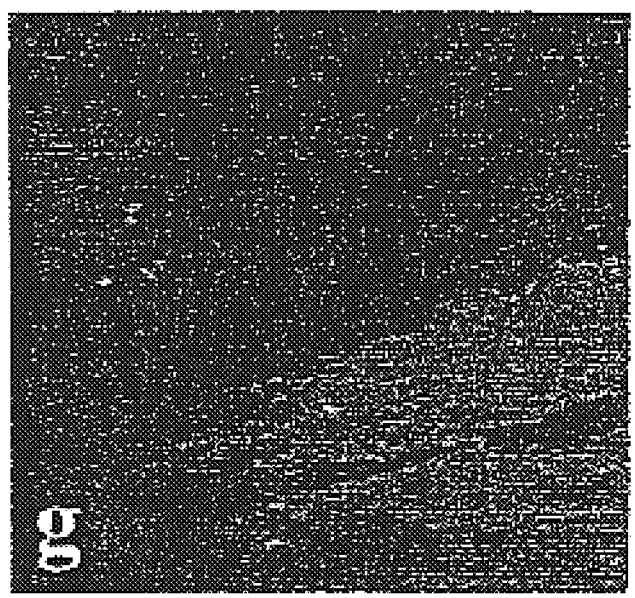
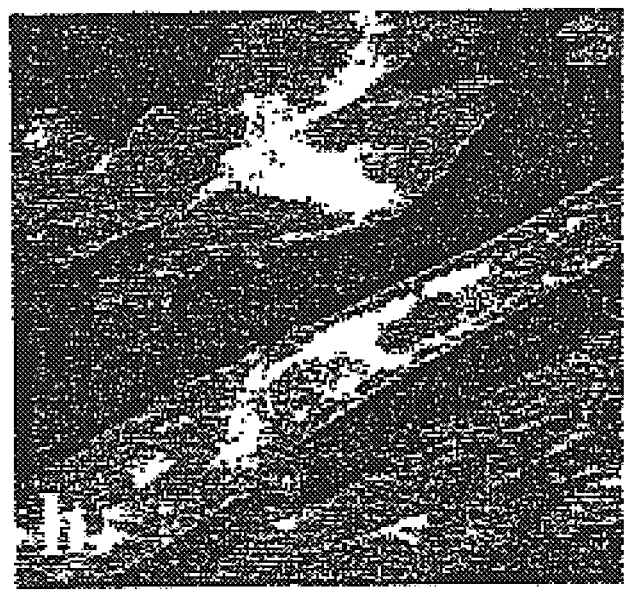

Fig.2 B XLT Suite
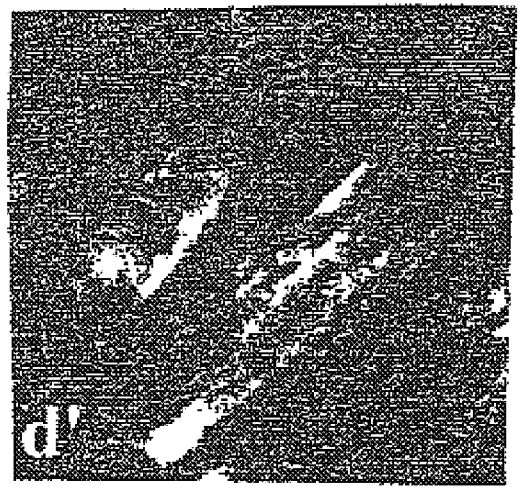
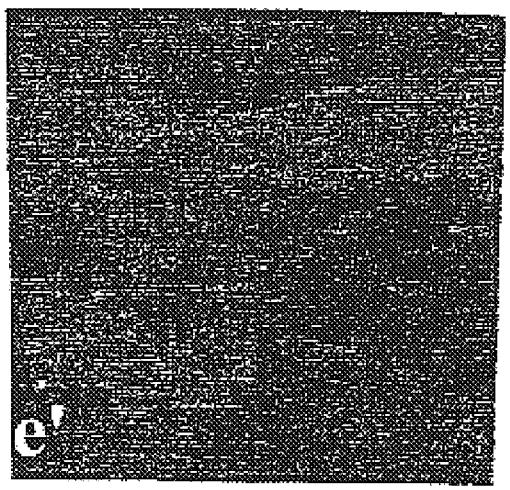
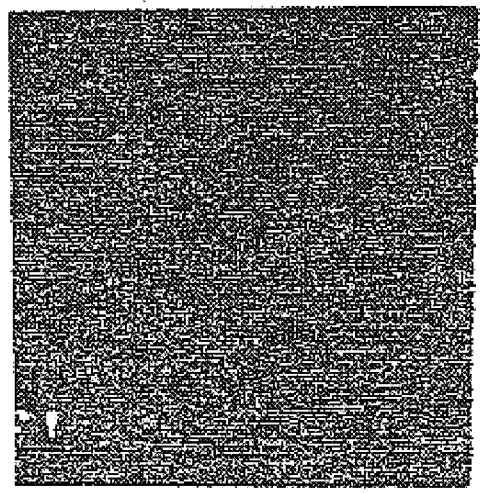

Fig.2 B XLT Suite
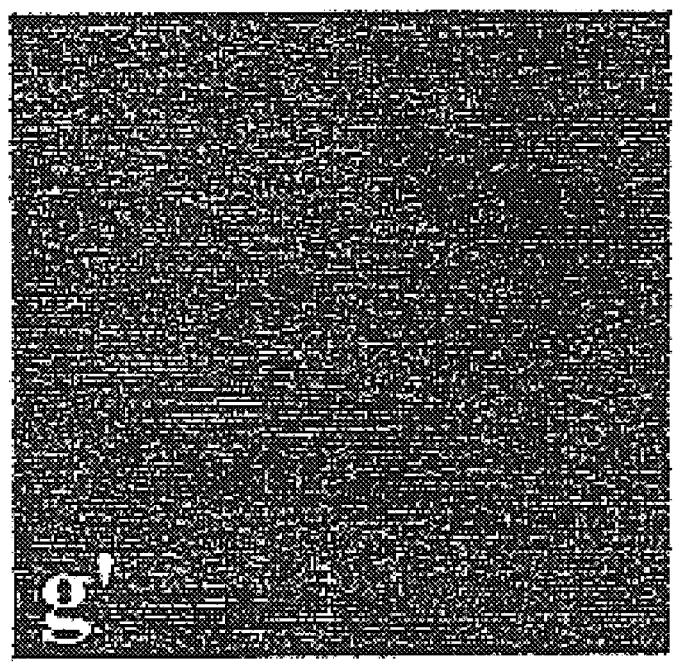
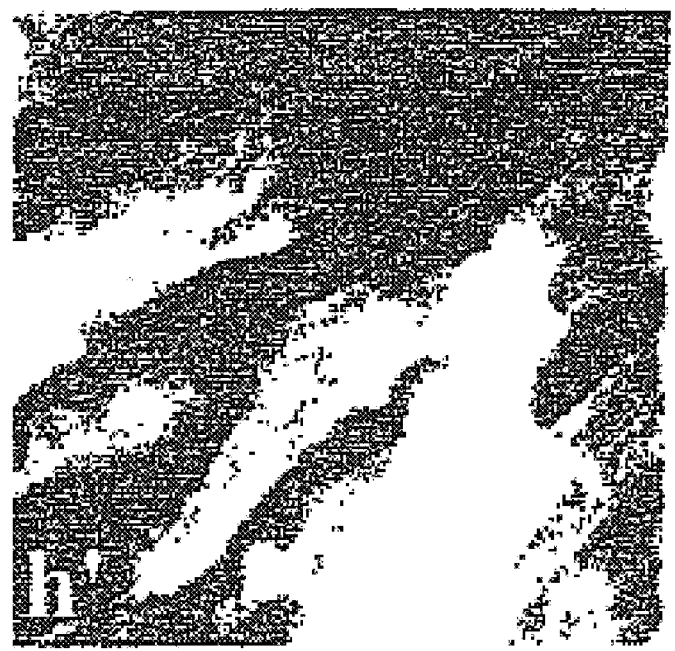

COMPOSITION AND METHOD FOR AUGMENTING OR RESTORING THE PRODUCTION OF FETAL PROTEIN IN PATIENT IN NEED THEREOF

RELATED APPLICATIONS

This application is a continuation-in-part of U.S. application Ser. No. 10/009,198, filed on Jun. 10, 2002, which is a national stage filing under 35 U.S.C. § 371 of International Application No. PCT/FR00/01612, filed on Jun. 9, 2000; the entire contents of which are hereby incorporated by reference. This application also claims priority under 35 U.S.C. §§ 119 and/or 365 to application Ser. No. 99/07442, filed in France on Jun. 11, 1999; the entire content of which is also hereby incorporated by reference.

BACKGROUND OF THE INVENTION

The present invention relates to methods and compositions for prevention and/or treatment of diseases or conditions caused by deficiency in the adult isoform of a given protein, such as occurs in dystrophies or thalassemia and sickle-cell diseases, wherein said methods comprise administering to a patient in need thereof a composition containing NO or at least one compound able to release or induce NO formation in cells, said administration resulting in augmenting or restoring the production of the fetal isoform of said protein. More specifically, the present invention is directed to a method for inhibiting or reversing the switching from production of fetal to adult isoform of a given protein, thus augmenting or restoring the production of said fetal protein in patient in need thereof. In particular, the present invention is directed to a method for controlling the fetal protein switch by administering to a patient in need a composition containing NO or at least one compound able to release or induce NO formation in cells.

It is known that in mammals, and particularly in humans, including those having the genetic mutations cited below, during fetal development, the fetus produces a fetal hemoglobin which comprises, instead of beta-globin proteins, two gamma-globin proteins. At some point during fetal development or infancy, depending on the particular species and individual, there is a so-called "globin switch" whereby the precursors of erythrocytes in the fetus switch from making predominantly gamma-globin to making predominantly beta-globin. Normal adult hemoglobin comprises a molecule with four polypeptide chains, two of which are designated alpha-subunits and two of which are designated beta-subunits. Diseases known as sickle cell syndromes and thalassemia are associated with genetic mutations in the beta-chain of the haemoglobin. Several treatments of beta-thalassemia have been proposed using chelator or polyanionic amine (for a review, see Rund and Rachmilewitz, 2000, Crit. Rev. Oncol. Hematol., 33:105–118). Alternatively, based on the observation that increased levels of fetal gamma-globin ameliorate the severity of sickling disorders, it has been proposed to re-induce the silent fetal gamma-globin gene in affected patient by administering chemotherapeutic agents (such as hydroxyurea and 5-azacytidine), growth factors (erythropoietin), cytosine arabinoside or butyric acid and butyrate derivatives (for review, please refer to Swank and Stamatoyannopoulos, 1998, Cur. Op. Gen. and Dev., 8:366–370; Rund and Rachmilewitz, 2000, Crit. Rev. Oncol. Hematol., 33:105–118). More specifically, works conducted on sickle-cell disease and thalassemia have demonstrated that hydroxyurea and butyrate are able to reactivate the expression of the fetal gene of hemoglobin. This result could, at least in part, be explained by common metabolic phenomena. The urea and Krebs cycles are coupled together and if hydroxy-urea interferes with the urea cycle, it could lead to retro-regulation of the Krebs cycle, which would cause a lower consumption of acetyl-CoA and therefore the formation of ketone bodies such as beta-hydroxybutyrate. Nevertheless, while said type of compounds might ameliorate the clinical conditions in beta-thalassemia patient, these treatments are not yet enough satisfactory in terms of efficiency or toxicity. Thus, there is still a need for an ideal agent which would be one that is readily available, economically affordable, effective and safe even with chronic use.

Similarly, Duchenne muscular dystrophy (DMD) and Becker muscular dystrophy (BMD) are allelic, lethal degenerative muscle genetic diseases wherein mutations in the dystrophin gene on chromosome x result in the absence of dystrophin, a cytoskeletal protein, under the sarcolemmal membrane in skeletal and cardiac muscle (DMD) or in a reduced level and/or in expression of a shorter, internally deleted form of dystrophin (BMD). Moreover, there exists a fetal isoform of dystrophin expressed at the fetal stage, the utrophin. However, Mizuno et al. (1993, J. Neurol. Sci., 119:43–52) have shown that utrophin is found in the muscles in both MD patients and in adult controls indicating that expression of the corresponding utrophin gene is not fully switch off during development. Actually, the difference between fetus and adult utrophin is its localisation: it is no longer found in the sarcolemma of adult tissue where it is replaced by dystrophin, but it still persists in satellite cells, the neuromuscular junctions and the capillaries. More specifically, in normal muscle fibres, utrophin accumulates selectively at the postsynaptic membrane of the neuromuscular junction where its precise physiological role remains to be determined. Several strategies have been envisaged to counteract the effects of dystrophy, including pharmacological treatment with gluco-corticoids, myoblast transplant and gene therapy (De La Porte et al., 1999, Int. Rev. Cytol., 191:99–148). Upregulation of utrophin has also been proposed as a therapeutic approach via increased expression of utrophin. Previous data have shown that utrophin is able to perform the same cell functions as dystrophin and would therefore be able to compensate for the absence of dystrophin (Blake et al., 1996, Brain Pathol., 1:37–47; Campbell and Crosbie, 1996, Nature, 384:308–309; Deconinck et al., 1997, Nature Med., 3:1216–1221; Tinsley et al., 1998, Nature Med., 4:1441–1444). According to said strategy, if utrophin can be systematically extended from the synaptic regions of dystrophic muscle fibres into extrasynaptic compartments, preferably at the sarcolemma level, it may functionally compensate for the lack of dystrophin or related activity, and thus restore muscle functions. Enhanced utrophin production has been previously obtained in regenerating fibres (i.e., in inflammatory conditions; Helliwell et al., 1992, Neuromuscul. Disord., 2:177–184; Mizuno et al., 1993, J. Neurol. Sci., 119:43–52) or by acting on molecules expressed at the neuromuscular junction, i.e., the neural agrin and heregulin (Gramolini et al., 1997, J. Biol. Chem., 272:8117–8120; Gramolini et al., 1998, J. Biol. Chem., 272:736–743). Nevertheless, even based on said up-regulation of utrophin strategy, no safe and effective therapies for these diseases are available at this time. Therefore, the technical problem underlying the present invention is the provision of improved methods and means for inhibiting or reversing the switching from production of fetal to adult isoform of a given protein, thus augmenting or restoring the production of said fetal protein in patient in need thereof, and preferably in augmenting or restoring said production at targeted site. This technical problem is solved by the provision of the embodiments as defined in the claims.

DETAILED DESCRIPTION OF THE INVENTION

The inventors have analyzed previous data related to metabolic phenomena associated with the expression of fetal genes and concluded that they relate to a low oxidizing metabolism and high glycolysis. Moreover, histochemical analysis of fetal muscle fibres have shown that the glycolytic enzymes are more expressed than the oxydizing enzymes. In addition, it has been shown that the mode of nitrogen secretion in the embryo is rather ammonotelic than ureotelic, illustrating a slowed functioning of the urea cycle. Based on said assumption, the inventors have imagined that, in said conditions, L-arginine, which is an essential substrate for the urea cycle, could be deviated towards other routes such as the NO-synthase (NOS) or amidinotransferase routes, hence leading to an increase in nitric oxide and creatine levels in the embryo. The understanding of these metabolic phenomena has led them to reproduce artificially this metabolic situation in adult animals and cultured cell systems for augmenting or restoring the production of fetal genes in adult tissues such that the presence and localisation of fetal proteins can be restored.

First, the present invention relates to a method for prevention and/or treatment of diseases or conditions caused by deficiency in the adult isoform of a given protein wherein said method comprises administering to a patient in need thereof a composition containing NO or at least one compound able to release, induce and/or promote NO formation in cells, said administration resulting in augmenting or restoring the production of the fetal isoform of said protein in said patient.

According to the present invention, "patient in need" designates patient which according to his stage of development should normally express adult isoform of the considered protein; thus it designates adults as well as infants or teenagers. Preferably said patient is human.

According to the present invention, "adult isoform" or "fetal isoform" of a given protein are designating the isoform of said protein which is mainly expressed in tissues of healthy patient at (i) the adult or (ii) the fetal and/or embryonic stage of development, respectively. "Mainly expressed" means that one isoform (i.e., "adult" or "fetal") is, at the considered stage of development (i.e., (i) adult or (ii) fetus/embryonic stage), present in the patient tissues at a higher amount compared to the other isoform (i.e., "fetal" or "adult," respectively); in specific case, the respective isoforms are not co-existing in the patient tissues at one special stage of development (i.e., (i) adult or (ii) fetus/embryonic) or are co-existing in the patient tissues but at distinct localizations. Preferred examples of "adult/fetal isoforms" couples are dystrophin/utrophin, delta-globin/gamma-globin, alpha-globin/gamma-globin and beta-globin/gamma-globin.

According to the present invention, "deficiency in the adult isoform of a given protein" means that said adult isoform, in said patient in need, is totally missing, is present in insufficient amount for permitting its functioning, is mutated (for example by deletion, insertion, substitution and/or modification of amino acids) and/or is non functional. Examples of such deficient adult isoforms are provided in papers related to mutations in dystrophin which cause Duchenne and Becker muscular dystrophies (Hoffman et al., 1987, Cell, 51:919–928; mutations in the extracellular matrix protein laminin 2) (Helbling-Leclerc et al., 1995, Nature Genet., 11:216–218; Allamand et al., 1997, Hum. Mol. Genet., 6:747–752; mutations in each of alpha-, beta-, gamma-, and delta-SG causing autosomal recessive LGMD types 2D, 2E, 2C, and 2F, respectively) (Roberds et al., 1994, Cell, 78:625–633; Piccolo et al.,1995, Nature Genet., 10:243–245; Lim et al., 1995, Nature Genet., 11:257–265; mutations in alpha, beta, delta chain of globin) (Clarke and Higgins, 2000, Clin. Chem., 46:1284–90).

According to the invention, "diseases or conditions caused by deficiency in the adult isoform of a given protein" designates all diseases or conditions resulting from absence, insufficient amount, mutation (for example by deletion, insertion, substitution and/or modification of amino acids) and/or non-functionality of the adult isoform of a given protein as indicated above. Preferably, according to the present invention, it designates hereditary diseases such as dystrophies including Duchenne and Becker muscular dystrophies; sickle cell diseases including diseases which cause sickling of the red blood cells and sickle cell anemia (which results from two hemoglobin S genes), sickle beta-thalassemia (one hemoglobin S and one beta-thalassemia gene), and hemoglobin SC disease (one hemoglobin S and one hemoglobin C), and the somewhat rare disease hemoglobin C Harlem; thalassemia including alpha-thalassemia and beta-thalassemia.

As used herein, "NO" means invariably nitric oxide or nitrogen oxide. It refers to uncharged nitric oxide, as well as negatively charged nitric oxide (i.e., nitroxyl ion, $NO^-$) and positively charged nitric oxide (i.e., nitrosonium ion, $NO^+$). It can be provided by gaseous nitric oxide however because of the somewhat cumbersome nature of said delivery, preferably NO is provided indirectly by compounds which generate NO or related N-oxide species, directly or indirectly, i.e., "compounds able to release, induce and/or promote NO formation in cells." Examples of said compounds are widely called the NO donors; furthermore, said class of compounds encompasses precursor of nitric oxide, i.e., substrates of NO synthase (NOS) which are metabolized in cells and thus induce NO formation, preferred example is L-Arginine (2-amino-5-guanidinovaleric acid) or its derivatives such as hydroxy-arginine or its boron derivatives. NO due to its chemical and biochemical properties has been implicated in a wide variety of bioregulatory processes, including the physiological control of blood pressure, macrophage-induced cytostasis and cytotoxicity or neurotransmission, modulation of cellular and physiological processes to limit oxidative injury, limitation of processes such as leukocyte adhesion, protection against cell death mediated by $H_2O_2$, alkylhydroperoxides and xanthine oxidase (for a review, see Wink et al., 2001, Antioxid Redox Signal, 3:203–13). Thus numerous pharmacological applications have been disclosed using NO or NO donors as pharmaceutical tools (for examples, see WO 96/02241, WO 99/01427, WO 97/25984, WO 01/70199). For example, they have been used as vasodilator in sickle cell disease (Atz and Wessel, 1997, Anesthesiology, 87:988–990), for increasing the affinity of haemoglobin for oxygen (U.S. Pat. No. 5,885,621; Head et al., 1997, J. Clin. Invest., 100:1193–1198). "NO donors" are well known by those skilled in the art (see for example Feelisch, 1998, Naunyn-Schiedeberg's Arch Pharmacol, 358:113–122). As disclosed in said revue, known examples of NO donors are organic nitrates ($RONO_2$s) (e.g. glyceryl trinitrate, pentaerythrityl tetranitrate, isosorbide dinitrate or isosorbide 5-mononitrate), S-nitrosothiols (RSN Os) (e.g. S-nitrosoglutathione or GSNO, S-nitroso-N-acetyl-DL-penicillamine or SNAP and S-notrosoalbumin), sydnonimines (e.g. N-ethoxycarbonyl-3-morpholino-sydnonimine or molsidomine and 3-morpholino-sydnonimine or SIN-1), NONOates, sodium nitroprusside or potassium pentachloronotrosylruthenium. Additionally, the invention extends to the use of NO donors or compounds involved in metabolic pathways enabling an increase in the cell production of NO.

According to a first preferred embodiment, the method of the invention relates to a method for prevention and/or treatment of diseases or conditions caused by deficiency in dystrophin wherein said method comprises administering to a patient in need thereof a composition containing NO or at least one compound able to release or induce NO formation in cells, said administration resulting in augmenting or restoring the production of utrophin in said patient.

The work conducted under the present invention has shown that in cultured myotubes, L-arginine and NO donor compounds increase both the level and the membrane localisation of utrophin. It has further been shown that after injection of L-arginine in the muscles, the localisation of utrophin at the membrane of the muscle fibre occurs in control mice and increases in mdx mice (which show natural, low expression of utrophin). Thus, the present invention has shown that the injection of a pharmaceutical composition containing NO or at least one NO donor (i.e., a compound able to release, promote or induce NO formation in the cells) makes it possible to induce the onset of utrophin, notably at the sarcolemma, of dystrophic and normal muscles.

Consequently, the invention especially concerns the use of NO and/or at least a NO donor compound (i.e., able to release, promote and/or induce NO formation in cells) to prepare a pharmaceutical product for the re-expression of the fetal isoform of a given protein in patient who is deficient for the adult isoform of said protein. More particularly, according to the method of the invention, it is possible to reactivate the expression of utrophin in adult tissues such as to restore the presence and localisation of this protein at the sarcolemma, so that utrophin replaces dystrophin, whenever the latter is absent.

Thus, according to another preferred embodiment, the method of the invention relates to a method for restoring the presence and localisation of utrophin at the sarcolemma of muscles in the treated patient. In preferred embodiments, said muscles are skeletal muscles (e.g. striated muscles) including the one of diaphragm, arms, legs (soleus, tibialis, gastrocnemius, etc.), cardiac muscles or smooth muscles.

According to another preferred embodiment, the method of the invention relates to a method for prevention and/or treatment of diseases or conditions caused by deficiency in hemoglobin wherein said method comprises administering to a patient in need thereof a composition containing NO or at least one compound able to release or induce NO formation in cells, said administration resulting in augmenting or restoring the production of gamma-globin in said patient. In most preferred embodiment, said method method relates to diseases or conditions caused by deficiency in beta-globin.

Thus, the treatment method of the invention may be an alternative to the previously disclosed pharmaceutical approaches and may be used in place of hydroxyurea or butyrate in the frame of treatment of thalassaemia and sickle-cell disease.

It is also an object of the present invention to provide a method for inhibiting or reversing in a patient, preferably in a fetus or an infant, the switching from production of fetal to adult isoform of a given protein, thus augmenting or restoring the production of said fetal protein in those individuals with diseases or conditions caused by deficiency in the adult isoform of a given protein (e.g. dystrophies, sickle cell syndromes or thalassemias).

In particular, the present invention is directed to a method for controlling (i.e., inhibiting, activating or reversing) the fetal protein switch by administering to a patient in need a composition containing NO or at least one compound able to release, promotes or induce NO formation in cells.

"Controlling (i.e., inhibiting or reversing) the fetal protein switch" means that the levels of the fetal isoform of a given protein in non treated patient is lower from the one observed after his treatment with the compounds of the invention. According to preferred embodiment, treatment of the patient with the compounds of the invention leads to augmenting or restoring the production of fetal isoform in said patient, preferably to restoring the presence and localization of the fetal isoform in particular tissues, in the treated patient compared to the fetal isoform level observed before said treatment.

While it is possible to utilize the compounds of the invention in vivo per se, it is preferable to present them as a pharmaceutical formulation preparation containing at least one active compound and at least one pharmaceutically acceptable carrier. The carriers must be acceptable in the sense of being compatible with other ingredients of the formulation and not deleterious to the recipient. In preparing such a composition, any conventional pharmaceutically acceptable carrier can be utilized. The carrier material can be an organic or inorganic inert carrier material suitable for the selected route of administration. For example, the formulation may comprise a pharmaceutically acceptable injectable carrier (for examples, see Remington's Pharmaceutical Sciences, $16^{th}$ ed. 1980, Mack Publishing Co). The carrier is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g. Tris-HCl, acetate, phosphate), emulsifiers, solubilizers or adjuvants. The pH of the pharmaceutical preparation is suitably adjusted and buffered in order to be useful in in vivo applications. Suitable carriers include water, gelatin, gum arabic, lactose, starch, magnesium stearate, talc, vegetable oils, polyalkylene-glycols, petroleum jelly and the like. Furthermore, the pharmaceutical formulation may contain other pharmaceutically active agents. Additional additives such as flavoring agents, preservatives, stabilizers, emulsifying agents, salts for varying the osmotic pressure, buffers and the like may be added in accordance with accepted practices of pharmaceutical compounding. Any conventional form such as tablets, capsules, pills, powders, granules, and the like may be used. Advantageously, they are in the form of tablets, sugar coated tablets, hard gelatin capsules, capsules, granules, for oral administration, or solutions or suspensions for administration via an injectable channel.

The formulations of the invention are preferably formulated and dosed in a fashion consistent with good medical practice taking into account the clinical condition of the individual patient, the cause of the condition in need of therapy, the site of delivery of the composition, the method of administration, the scheduling of administration, and other factors which will be ultimately at the discretion of the attendant physician. The "effective amount" for purposes herein is thus determined by such considerations.

The methods of the invention may be carried out by administering the formulation containing compounds of the invention by any route whereby drugs are conventionally administered. Such routes include systemic and local routes. Examples are intravenous, intramuscular, subcutaneous, intracranial, intraperitoneal, as well as oral routes. Preferably, the method of the invention is carried out via intramuscular, oral or intravenous routes of administration.

Typical formulations for administration would be sterile aqueous solutions including water/buffered solutions. Intraveneous vehicles include fluid, nutrient and electrolyte replenishers. Preservatives and other additives may also be present such as antibiotics and antioxidants. Formulations for i.v. or i.m. administration preferably contain from about 50 mg/liter to about 500 mg/liter of at least one compound described herein. The preferred oral dosage form is capsules or tablets containing from 50 to 500 mg of a derivative of the invention.

The frequency and dosages of administration of the above compounds will depend upon when the compound is introduced, whether the subject is a fetus, infant or adult, the size and weight of the subject, the condition of the patient, and the like. Generally, injections are beginning at a dosage of about 50 microg/kg to 10 mg/kg; and often as low as 50 microg/kg to 100 microg/kg body weight per day. Dosages, up to about 10 mg/kg/day may be utilized at the discretion of the physician. In one preferred embodiment of the invention, L-arginine is administered in the proportion of 200 mg/kg for 3 to 4 weeks.

Since apparently the switching process is not complete in humans until approximately four months after birth, treatment may be initiated after birth up until about the fourth month of infancy and continued as long as necessary to maintain enhanced fetal isoforrn levels in the patient, or treatment may be initiated later in childhood or adulthood. As a general proposition, the total pharmaceutically effective amount of the compounds administered parenterally per dose will be in the range of about 10 microg/kg/day to 200 mg/kg/day, preferably 50 microg/kg/day to 10 mg/kg/day of patient body weight, although, as noted above, this will be subject to a great deal of therapeutic discretion. The key factor in selecting an appropriate dose is the result obtained, as measured by inhibition of fetal to adult isoform switching or by other criteria as deemed appropriate by the practitioner.

The composition herein is also suitably administered by sustained release systems. Suitable examples of sustained release compositions include semi-permeable polymer matrices in the form of shaped articles, e.g., films, or microcapsules. Sustained release matrices include polymer films containing nitroso-compounds (Espadas-Torre et al., 1997, J. Am. Chem. Soc., 119:2321–2322), biodegradable polymer (U.S. Pat. No. 5,944,444 or U.S. Pat. No. 5,605,696), hydrophobic matrix (WO 01/70199), polylactides (U.S. Pat. No. 3,773,919, EP 58,481), copolymers of L.glutamic acid and gamma-ethyl-L-glutamate (Sidman et al., 1983, Biopolymers, 22:547–556), poly(2-hydroxyethyl methacrylate) (Langer et al., 1981, J. Biomed. Mater. Res., 15:167–277), ethylene vinyl acetate (Langer et al., Id.) or poly-D-3-hydroxybutyric acid (EP 133,938). Sustained release compositions also include liposomally entrapped compounds or a mixture thereof Such compositions are widely known in the art.

Generally, the formulations are prepared by contacting the compounds according to the present method uniformly and intimately with liquid carriers or finely divided solid carriers or both and then, if necessary, shaping the product into the desired formulation. Compounds for use in therapeutic administration must be sterile. Sterility is readily accomplished by sterile filtration through (e.g., 0.2 micron) membranes.

As further application of the compounds according to the present method, they may be added in vitro to cell cultures taken from patients and the amount of fetal (or alternatively of the adult) isomer of a given protein synthesis measured to determine the potential efficacy of further treatment for the treated disorders, such as dystrophy, thalassemia or sickle cell disease. The compounds may be thus used in vitro in cell cultures from patients to determine whether further addition of one of the compounds would result in continued inhibition or reversal of the fetal iso form switch.

More particularly, the invention concerns the use of NO, of a NO donor compound or of a compound able to release, promote or induce NO formation in cells, to prepare a medicinal product intended to reactivate the expression of at least one fetal gene in adult tissues such as to restore the presence and/or localization of at least one fetal protein.

The use according to the invention makes it possible to reactivate the fetal situation by re-expressing the embryonic form of the protein encoded by the deficient gene.

Some compounds such as hydroxyurea or beta-hydroxybutyrate are toxic or ill-tolerated, therefore the invention more particularly concerns, as compound able to induce NO formation, either L-arginine or its derivatives such as hydroxy-arginine or its boron derivatives which promote NO production or substrate preservation.

The invention therefore also concerns a pharmaceutical composition containing NO or at least a NO donor compound or a compound able to release, promote or induce NO formation in the cells, associated in said composition with a pharmaceutically acceptable vehicle.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the claims, the invention may be practiced otherwise than as specifically described.

All of the above cited disclosures of patents, publications and database entries are specifically incorporated herein by reference in their entirety to the same extent as if each such individual patent, publication or entry were specifically and individually indicated to be incorporated by reference.

BRIEF DESCRIPTION OF THE DRAWINGS

Other features and advantages of the invention are given in the following examples, wherein reference is made to FIGS. 1 and 2, wherein respectively:

FIG. 1 shows the occurrence of utrophin under the sarcolemma of normal adult mice and mdx mice chronically treated with L-arginine (magnification ×300). FIG. 1 shows the immunolocalisation of utrophin on the muscle membrane of normal mice and mdx mice treated with L-arginine. (a) control corresponding to normal mice given an injection of physiological serum: no utrophin observed at the sarcolemma. (b) normal mice treated with the L-arginine: utrophin is seen under the sarcolemma. (c) control corresponding to the mdx mice given an injection of physiological serum: utrophin is visible at the sarcolemma. (d) mdx mice given L-arginine: increase in utrophin levels under the sarcolenima.

FIG. 2: shows the variation of utrophin in the myotubes after treatment involving nitric oxide (NO) (magnification ×200). A, a–h: normal cell line (NXTL). B, a'–h': mdx cell line (XLT). The cell cultures were treated by exposure of the differentiated myotubes to drugs for 48 hours. A, a': control cultures. B, b': L-arginine(2.10$^{-3}$M). c, c': SIN-1 (10$^{-3}$ M). d, d': SIN-I (10$^{-3}$ M) +L-arginine (10$^{-3}$ M). e, e': D-arginine (10$^{-3}$ M). f, f': L-arginine (10$^{-3}$ M)+OQD (10$^{-5}$ M). g, g': L-NMMA (10$^{-3}$ M). h, h': hydroxyurea (10$^{-4}$ M).

EXAMPLES

1. Introduction

Figure 3:
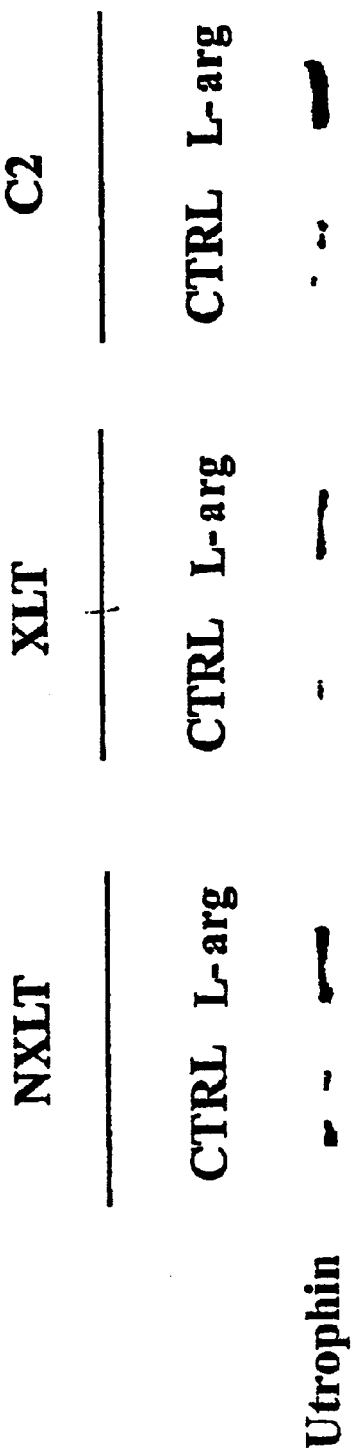
FIG. 3: shows the increase in utrophin levels in NXLT, XLT and CT myotubes under the action of L-arginine. Imunoblot analysis of utrophin was conducted under control conditions (CTRL) and after 48 hours treatment with 2.10$^{-3}$ M L-arginine (L-arg).

The most frequent DMD (Engel et at., 1994, Dystrophinopathies in: Myology (McGraw-Hill, Inc.) 2:1133–1187) (1 out of 3500 boys) and the most severe myopathy is characterized by gradual loss of muscular strength, finally leading to marked fibrosis and fatty infiltration. The DM0 gene (Monaco et al., 1986, Nature, 323:646–650) spans approximately 2300 kb on band p21, and most DM0 mutations are intragene deletions, leading to the absence of dystrophin, a protein of 427 kD, in patient muscle (Ahn et al., 1993, Nat. Genet., 3:283–291; Hoffman et al., 1987, Cell, 51:919–928). Dystrophin is a large protein of the cytoskeleton localized on the inner surface of the sarcolemma of normal muscle. Dystrophin is associated with a complex of glycoproteins and membrane proteins respectively called DAGs for "dystrophin-associated glycoproteins" and DAPs for "dystrophin-associated proteins" which are considerably reduced in the muscle of patients suffering from DMD (Appel et al., 1995, Neuron, 15:115–126; Ozawa et at., 1995, Hum. Molec. Genet., 4:11711–11716). One of the proteins, syntrophin, is associated with NOS via a PDZ domain (Brenman et al., 1996, Cell, 84:757–767). The dystrophin-glycoprotein complex binds the subsarcolemmal cytoskeleton to the extracellular matrix. Dystrophin is involved in maintaining the morphological and functional structure of striated muscle fibre and in calcium homeostasis.

An autosomal transcript of 13 kb encoded by a gene of the long arm of chromosome 6 in man and chromosome 10 in mice, has been identified. It encodes a protein having more than 80% homology to dystrophin, called utrophin, of 395 kD (Love et al., 1989, Nature, 339:55–58; Tinsley and Davies, 1993, Neuromusc. Disord., 3:537–539). The homology between dystrophin and utrophin extends along their entire length suggesting that they derive from a common ancestral gene. Utrophin, like dystrophin, binds to actine via the N-terminal domain, and C-terminal domain is highly conserved. Utrophin is associated with a complex of sarcolemmal proteins that are identical or at least antigenically similar to those of dystrophin. Its localization is the same as that of the acetycholine receptor, at the top of the post-synaptic folds. Utrophin is perhaps one of the molecules of the cytoskeleton which organizes and stabilizes the cytoplasmic domain of the acetylcholine receptor.

Patients suffering from DM0 and Becker dystrophy (a less severe form of DM0) and mdx mice maintain some expression of utrophin at the sarcolemma (Takemitsu et al., 1991, Biochem. Biophys. Res. Comm., 180:1179–1186; Koga et al., 1993, Biochim. Biophys. Acta, 1180:257–261.) probably to compensate for the absence of dystrophin. The methods for post-regulating expression of the utrophin gene are beneficial to muscle function. For example, the use of the transgenic expression firstly of truncated utrophin and then of full-length utrophin in mice led to demonstrating that utrophin can functionally replace dystrophin (Deconinck et al., 1997, Nature Medline, 3:1216–1221): the overexpression of utrophin leads to the restoration of all the components of DAGs, and muscle performance is increased. The overexpression of utrophin saves the deterioration of the diaphragm, the most severely affected muscle in mdx mice. Also utrophin-deficient mice show a phenotype of slight myopathy, like mdx mice with dystrophin deficiency, but mice with both dystrophin and utrophin deficiency show severe myopathy of the skeletal and cardiac muscles. The expression of a transgene of truncated utrophin in the muscles of mice with both dystrophin and utrophin deficiency, gives protection against death and the development of any clinical phenotype.

During the development stage, utrophin is found on the membrane surface of immature fibres in normal embryos and is gradually replaced by dystrophin, except at the neuromuscular junction where it persists (Oliver et al., 1996, NeuroReport, 7:924–926). Therefore, it is possible to consider utrophin as the fetal homologue of dystrophin. Several observations have brought to light the mechanism which governs the changeover from the fetal gene to the adult gene. Patients suffering from sickle-cell disease or thalassaemia who have an abnormal adult haemoglobin gene, were treated with butyrate or hydroxyurea which reactivated the fetal haemoglobin gene (Rodgers et al., 1993, New England Journal of Medicine, 328:73–80; Olivieri and Weatherall, 1998, Hum. Mol. Genet., 7:1655–1658; Perrine et al., 1993, New England Journal of Medicine, 328:81–86). It is possible to expect a high level of glycolysis in the fetus with preferential movement of acetyl-CoA towards the anabo tic routes. Low oxydizing phosphorylation should promote acetyl-CoA pathways to the ketone bodies. The subsequent accumulation of beta-hydroxybutyrate could then induce the expression of the fetal genes. Since the Krebs cycle and the urea cycle are coupled, low oxydizing phosphoryiation is correlated with low urea production, which may also be induced by treatment with hydroxyurea. This could result in high levels of L-arginine which could therefore be used as substrate for NOS and amidinotransferase leading to creatine. Nitric oxide (NO) would then give the signal for the expression of fetal genes which would therefore be responsible for the high levels of creatine found in the urine of patients suffering from DM0. The mechanisms envisaged above by the inventors led them to testing the effects of L-arginine and NO donor compounds on the expression of utrophin. The inventors were therefore able to show in remarkable manner that in normal adult mice and in mdx mice treated chronically with L-arginine, which is a substrate of NOS, the levels of muscle utrophin increased at the membrane along the entire length of the sarcolemma. The experiments reported below show in surprising manner that the treatment of NO donors with L-arginine increases the levels of utrophin and its membrane localisation in normal and mdx cultured myotubes. Similar results were obtained with hydroxyurea which was used as a control, as it is known that this product activates fetal haemoglobin.

2. Methods

2.1 Treatment of Mice

Three normal, adult mice aged 18 months (C57 BL/6 line) and three mdx mice were given a daily intra-peritoneal injection of 200 mg/kg L-arginine for three weeks. Two other groups of three adult mice were used as controls and were given a daily injection of physiological serum.

The mice were sacrificed by ether anaesthesia, the biceps femoris and the semi-tendinous muscles were quickly dissected from the hind limbs of each animal and frozen in liquid nitrogen.

2.2. Cell Culture

Myotubes were obtained from normal cell line (NXLT) and mdx cell line as described by Liberona et al (1998, Muscle & Nerve, 21:902–909), and C2 myotubes as described by Inestrosa et al. (1983, Exp. Cell Res., 147:393–405).

2.3. Immunofluorescence

In vivo. After cold fixing in methanol (−20° C. for 10 minutes) sections of 7 mm were incubated for two hours with utrophin specific monoclonal antibody (NCL-DRP 2, Novacastra) (1/10 vol/vol) in PBS containing 0.1% saponin and 0.2% bovine albumin. The second antibody labelled with fluoroscein (N 1031, Amersham) was diluted (1/4000 vol/vol) in PBS containing 0.1% saponin and incubated for one hour.

In vitro. The cultures were treated as described previously with the exception of the second antibody labelled with fluoroscein which was diluted to 1/100 vol/vol. The incubation time was 2 hours for the first and second antibody.

2.4. Immunoblotting

The myotubes obtained from the NXLT, XLT and C2 lines were homogenized using a Polytron (Kinematica) in 10 mM Tris-HCl pH 6.8, 1% Triton X-100, 1% SOS, 0.5% sodium deoxycholate on ice. The quantity of total proteins was determined following the protocol for the bicinchoninic acid protein test (BCA, Pierce). Equivalent quantities of protein were separated by SOS-Page on 5% gel, then electrotransferred onto a nitrocellulose membrane (Schleicher & Schuell). The membranes were then incubated with the same monoclonal antibody directed against utrophin used for the immunofluorescence techniques (1/250 vol/vol). The fixed antibodies were detected with a Sanofi anti-mouse goat secondary antibody (1/5000 vol/vol) bound to horseradish peroxydase and developed by chemioluminescence reaction (ECL, Amersham Pharmacy Biotech).

3. Results

The adult mice given an intraperitoneal injection of L-arginine for three weeks were sacrificed. After sacrifice, the thigh muscles were prepared by immunocytochemistry. After this treatment, utrophin was detected underneath the sarcolemma in the muscle fibres of normal mice as shown in FIG. 1a. Treatment of mdx mice with L-arginine increased the utrophin level already present in the sarcolemma (Takemitsu et al., 1991, Biochem. Biophys. Res. Comm., 180:1179–1186). Both in normal mice and in mdx mice, immunolabelling covers the sarcolemma and is present on part of the interstitial tissue. This labelling is probably due to the utrophin expressed by the capillaries and satellite cells.

This effect of arginine was then examined on cultured myotubes which are more suitable for direct application of drugs and avoids interference with non-muscular utrophin. The NXLT and XLT myotubes of normal and mdx mice respectively were used for immunochemical testing of the effects of L-arginine and NO on the expression of utrophin. After 48 hours treatment, utrophin labelling increased when the synthesis of endogenous NO was increased via excess L-arginine and when SIN-1 was applied as shown in FIG. 2. Utrophin was co-localized with the large clusters of acetylcholine receptors present on the myotubes evidencing that part of the labelling is membrane-related (not shown in the appended figure). The increased labelling of utrophin was also observed to a lesser extent on the cells of C2 mice myotubes and primary rat myotubes. The accumulated application of SIN-i and L-arginine further increases utrophin labelling as shown in FIG. 2. The absence of any effect by D-arginine illustrated in FIG. 2 demonstrates the involvement of NO in the method of the invention. The basal level of utrophin in the absence of NO-synthase activity shown in FIG. 2 was obtained after application of $N^G$-methyl-L-arginine (L-NMMA) which is an inhibitor of NOS. It is widely acknowledged that the intracellular effects of NO are mediated through the activation of soluble guanylate cyclase. The synthesis of utrophin induced by NO was inhibited in the presence of ODQ (Garthwaite et al., 1995, Mol. Pharmacol., 48:184–188) which is an antagonist specific to guanylate cyclase as shown in FIG. 2. FIG. 2 also shows that the hydroxyurea used by analogy with the treatment of thalassaemia, also increases utrophin labelling in remarkable manner. This effect probably arises from action on the expression of utrophin.

In order to complete the analysis of the effect of NO production on utrophin expression in normal and mdx mice, the inventors extracted the proteins from myotube cultures either treated or not treated with L-arginine under the same conditions as previously. The Western-blots in FIG. 3 show an evident increase of utrophin in both types of cell lines, thereby confirming imuunocytochemical data. This increase in utrophin after treatment with L-arginine was confirmed in a cell line of C2 myotubes (FIG. 3).

The work of the present invention was conducted for the purpose of treating patients suffering from Duchenne and Becker myopathies, or from thalassaemia and sickle-cell disease, using new fetal gene reactivation strategy. But the understanding of the metabolic phenomena described above can be used to transpose the latter to the treatment of any disease in which the deficient adult gene has a fetal homologue.

What is claimed is:

1. A method for treatment of a disease or condition caused by deficiency in dystrophin, wherein said method comprises administering to a patient in need thereof a composition containing nitric oxide (NO) or a NO donor, said administration resulting in augmenting or restoring the production of the corresponding fetal isoform named utrophin of said dystrophin in said patient, wherein said condition or disease is selected from the group consisting of Duchenne and Becker muscular dystrophies.

2. The method of claim 1, wherein said NO donor is selected from the group consisting of organic nitrates (RONO2S), S-nitrosothiols (RSNOs), sydnonimines, NONOates, sodium nitroprusside and potassium pentachloronotrosylruthenium.

3. The method of claim 2, wherein said NO donor is a sydnonimine selected from the group consisting of N-ethoxycarbonyl-3-morpholino-sydnonimine and 3-morpholino-sydnonimine.

4. The method of claim 1, wherein said NO donor is selected from the group consisting of L-Arginine (2-amino-5-guanidinovaleric acid) and its derivatives.

* * * * *